United States Patent
Oberst

US006268143B1

(10) Patent No.: US 6,268,143 B1
(45) Date of Patent: Jul. 31, 2001

(54) AUTOMATED HIGH THROUGHPUT E. COLI O157:H7 PCR DETECTION SYSTEM AND USES THEREOF

(75) Inventor: Richard D. Oberst, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/366,585

(22) Filed: Aug. 4, 1999

Related U.S. Application Data

(60) Provisional application No. 60/095,363, filed on Aug. 5, 1998, now abandoned.

(51) Int. Cl.[7] .................... C12Q 1/68; G01N 33/554; C12P 19/34
(52) U.S. Cl. ............... 435/6; 435/7.32; 435/91.2
(58) Field of Search .................. 435/6, 18, 91.2, 435/196, 805, 5, 91.1; 536/24.3, 23.7

(56) References Cited

PUBLICATIONS

Zhao et al., "A multiplex PCR for identifying Shiga–like toxin–producing *Escherichia coli* O157:H7," Letters in Applied Microbiology, 1997, vol. 24, pp. 172–176.*

Batt, Carl A., "Molecular Diagnostics for Dairy–Borne Pathogens," 1997, J. Dairy Sci, vol. 80, pp. 220–228.*

Louie et al., "Sequence heterogeneity of the eae gene and detection of verotoxin–producing *Escherichia coli* using serotype–specific primers," 1994, Epidemiol. Infect., pp. 449–459.*

Zhao et al., Cloning and nucleotide sequence of a gene upstream of the eaeA gene of enterohemorrahagic *Escherichia coli* 1057:H7.*

* cited by examiner

*Primary Examiner*—John S. Brusca
*Assistant Examiner*—Young Kim
(74) *Attorney, Agent, or Firm*—Benjamin Aaron Adler

(57) ABSTRACT

The present invention describes the development and evaluation of the sensitivity and specificity of a PCR-based 5' nuclease assay for presumptively detecting *E. coli* O157:H7 DNA. The specificity of the eaeA-based, 5' nuclease assay system was sufficient to correctly identify all *E. coli* O157:H7 strains evaluated, mirroring the previously described specificity of the PCR primers. The SZ-primed, eaeA-targeted, 5' nuclease detection assay was capable of rapid, semiautomated, presumptive detection of *E. coli* O157:H7 when $\geq 10^3$ CFU/ml were present in modified tryptic soy broth (mTSB) or modified *E. coli* broth (mEC), and when $\geq 10^4$ CFU/ml were present in ground beef-mTSB mixtures. Incorporating an immunomagnetic separation step (IMS), followed by a secondary enrichment culturing step and with DNA recovery, improved the detection threshold to $\geq 10^2$ CFU/ml.

7 Claims, 2 Drawing Sheets

AUTOMATED HIGH THROUGHPUT E. COLI O157:H7 PCR DETECTION SYSTEM AND USES THEREOF

CROSS-REFERENCE TO RELATED APPLICATIONS

This non-provisional applications claims benefit of priority of provisional application U.S. Ser. No. 60/095,363, filed Aug. 5, 1998, now abandoned.

FEDERAL FUNDING LEGEND

This invention was produced in part using funds obtained through USDA Grant No. 96-34359-2593. Consequently, the federal government has certain rights in this invention.

BACKGROUND OF THE INVENTION

1. Field of the Invention

The present invention relates generally to the fields of microbiology and molecular biology of E. coli. More specifically, the present invention relates to the development and evaluation of the sensitivity and specificity of a PCR-based 5' nuclease assay for presumptively detecting E.coli O157:H7 DNA and the uses of such assay.

2. Description of the Related Art

Enterohemorrhagic Escherichia coli O157:H7 is an important human pathogen that is predominantly associated with hemorrhagic colitis and the more severe complications of hemolytic uremic syndrome. Although human to human transmission of E. coli O157:H7 has been demonstrated (25), most infections have been associated with the consumption of contaminated ground beef, milk, water, produce, and apple juice products that have been improperly handled, stored, or cooked (1,5,7,15,18,19,25,43). The primary reservoir is believed to be cattle (24,27). However, a clear understanding of the farm ecology of E. coli O157:H7 is lacking, partly because of the low detected prevalence in individual cattle and herds (20,40,55) and the low infectious dosage required for human infections (25,53).

Established methods for recovering and identifying E. coli O157:H7 from foods and feces have been hindered by the inability to specifically and rapidly detect small numbers of organisms from complex matrices and background microflora. Although the inclusion of pre-enrichment incubations and immunomagnetic separation (IMS) (6,9,11,16,22,31,44, 48) and additional selective subculturing or secondary enrichment incubations (12,14,30) have been reported to increase the detection rate of E. coli O157:H7 from foods and fecal specimens, these methods are dependent on isolating individual colonies from selective and/or indicator media and then characterizing them in immunological and biochemical/fermentation reactions. Immunological assays are used to determine if the O157 somatic and H7 flagellar antigens are present, while the biochemical/fermentation reactions determine the genus and species of the isolate in classical taxonomic fashion. Combined with the initial replication steps in the isolation process, the current E. coli O157:H7 identification process takes upwards of 5 or more days to complete. This adds considerably to the costs required to determine whether a sample contains E. coli O157:H7, and is a limiting factor in doing more E. coli O157:H7 tests.

Rapid methods for identifying E. coli O157:H7 in foods or fecal specimens have been directed at immunological or genetic targets. Antigenic targets have included the E. coli somatic (O157) or flagellar (H7) antigens (21,50); and two low-molecular-weight antigens (30,45); and the virulence-associated Shiga-like toxins (SLT) type I and II (3,17,33). However, these assays are occasionally unable to distinguish certain other E. coli strains from E. coli O157:H7 strains (30,49) and/or toxigenic from nontoxigenic E. coli O157 strains (46).

PCR-based detection procedures have been used to identify E. coli O157:H7 and have targeted the sltI and sltII genes (32,47,54); the EHEC uidA gene (10); and a portion of a 60-MDa plasmid (23). Because similar genes are present in some nonpathogenic E. coli and in other bacteria, individual PCRs that target these genes are unable to confirm the identity of an isolate as E. Coli O157:H7. Identification by PCR requires that multiple genes be targeted in separate PCRs on the DNA from a suspect organism or that the DNA from that organism be subjected to a multiplex PCR that targets the multiple genes simultaneously (10,23,42,51).

Presumptive identification of E. coli O157:H7 is possible in an individual, non-multiplexed PCR, if the reaction targets the EHEC eaeA gene. In separate studies targeting two different regions of the eaeA gene, every E. coli O157:H7 reference strain evaluated demonstrated the predicted PCR product. Louie et al. (36) targeted the 3' end of EHEC eaeA gene, whereas Meng et al. (41) amplified a 633 bp product upstream of the 5' end of the EHEC eaeA gene using PCR primers SZ-I and SZ-II. Both reactions were limited as confirmatory PCRs for identifying E. coli O157:H7, because similar PCR products were evident with some E. coli O157:NM strains and some enteropathogenic E. coli O55:H7 and O55:NM strains (36,41).

Although PCR can amplify DNA molecules thousands-fold, the specifically amplified product must be detected in order to prove its presence and a variety of methods have been developed. The most common research application is by gel electrophoresis, however, it does not show specificity of the PCR product and lacks sensitivity. Southern blots or dot blot hybridizations with probes will demonstrate specificity of the PCR, but they require multi-step processing and add considerable time and expense to the detection process. Neither of these PCR detection processes is conducive to rapid, high-throughput, automated PCR detection schemes.

Recently, 5' nuclease assays (TaqMan™, PE Applied Biosystems, Foster City, Calif.) have been described that allow the automated PCR amplification, detection, and analysis of Salmonella spp. (13,38); Listeria monocytogenes (2,4); and SLT genes (28,54) in various foods. The 5' nuclease assay exploits the 5'→43' exonuclease activity of Thermus aquaticus DNA polymerase (29,37) to hydrolyze an internal TaqMan™ probe labeled with a fluorescent reporter dye and a quencher dye (34). For the intact probe, the quencher dye suppresses the fluorescent emission of the reporter dye because of its spatial proximity on the probe. During PCR, the probe anneals to the target amplicon and is hydrolyzed during extension by the Taq DNA polymerase. The hydrolysis reduces the quenching effect and allows for an increase in emission of the reporter fluorescence. This increase is a direct consequence of a successful PCR, whereas the emission of the quencher dye remains constant irrespective of amplification.

Because development of fluorogenic reporter signals occurs only with a successful PCR, detection of specific DNA sequences can be based on monitoring for an increase in reporter fluorescence following PCR with a fluorometer (ABI Prism™ Sequence Detection System, PE Applied Biosystems). The fluorometric data can be automatically read and interpreted using a 96-sample format and presented as "yes" or "no" conclusions as to the presence or absence of the DNA within 15 minutes of the completion of the PCR.

The prior art is deficient in the lack of fully automated and high sample throughput PCR-based *E. coli* O157:H7 amplification/detection system. The present invention fulfills this long-standing need and desire in the art.

SUMMARY OF THE INVENTION

The present invention describes the development and evaluation of the sensitivity and specificity of a 5' nuclease assay for amplifying and presumptively detecting *E. coli* O157:H7 DNA. Evaluation of the 5' nuclease assay included the comparison of two DNA extraction procedures for recovering *E. coli* O157:H7 DNA from pure broth cultures; from pure broth cultures immediately before IMS and then retrieved on sorbitol MacConkey agar supplemented with cefeximine and tellurite (CT-SMAC); from pure broth cultures following immunomagnetic separation step (IMS) plus 18 h secondary enrichment and then retrieved on CT-SMAC; and from spiked broth cultures containing ground beef.

The present invention is directed to a method of presumptively detecting *E. coli* O157:H7 using SZ-primed, eaeA-based 5' nuclease assay, comprising the steps of collecting a sample suspected to contain *E. coli* O157:H7; preparing an enrichment broth culture of the sample; extracting DNA from the culture; amplifying the DNA by PCR using *E coli* O157:H7-specific primers; detecting the sample for *E. coli* O157:H7 by adding a fluorogenic probe specific for *E. coli* O157:H7 to the same reaction tube where the DNA was amplified; and determining the presence or absence of *E. coli* O157:H7 DNA in the test sample. Preferably, the *E. coli* O157:H7-specific primers are SZ-I (SEQ ID NO: 1) and SZ-II (SEQ ID NO: 2). Preferably, the fluorogenic probe specific for *E. coli* O157:H7 targets the eaeA gene of *E. Coli* O157:H7 and is selected from the group consisting of-SEQ ID NO: 3 and SEQ ID NO: 4. More preferably, SZI-97 (SEQ ID NO: 3) is the optimal probe.

In one preferred embodiment of the present invention, the sample is selected from the group consisting of a fecal sample, a n environmental sample, a food sample, a veterinary sample and a medical diagnostic sample.

In a preferred embodiment of the present invention, the claimed method is automated and detects $\geq 10^2$ CFU/ml of *E. coli* O157:H7 from the test sample. Generally, the entire identification process including extracting, amplifying and detecting steps takes approximately 2.5 hours.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention an d therefore are not to be considered limiting in their scope.

DETAILED DESCRIPTION OF THE INVENTION

Figure 1:
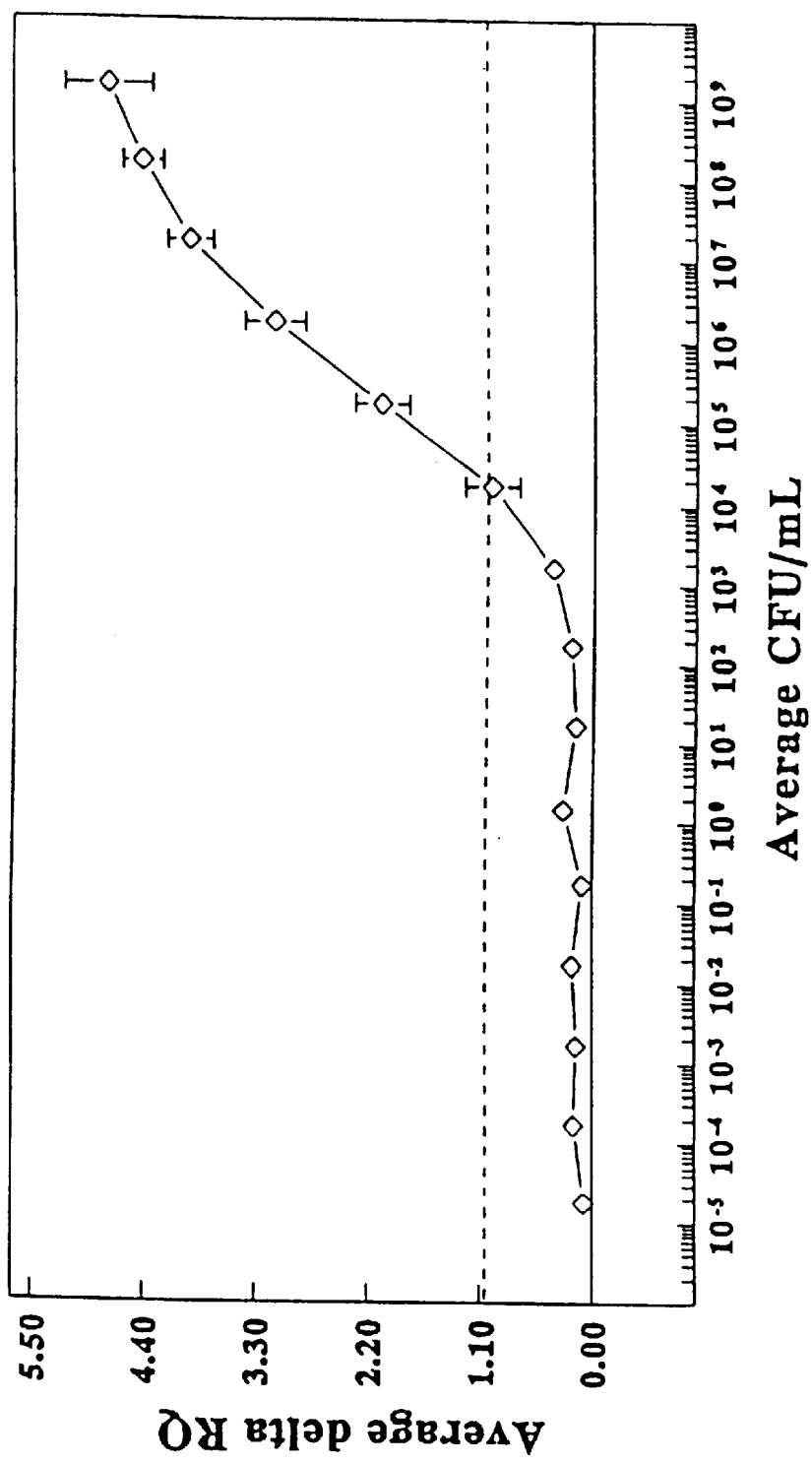
FIG. 1 shows sensitivity of the fluorogenic 5' nuclease assay for detecting *E. coli* O157:H7 in individual MicroAmp Optical Tubes and Caps (MOT) (Perkin-Elmer). Ten fold dilutions of *E. coli* O157:H7 were made in modified tryptic soy broth (mTSB) and modified *E. coli* broth (mEC) in triplicate. One millilter aliquots from each dilution were subjected to QIAamp Tissue Kit DNA recovery, and 5 μl of the recovered DNA solution was PCR amplified using the SZ-I (SEQ ID NO: 1) and SZ-II (SEQ ID NO: 2) primers in the presence of the SZI-97 fluorogenic probe. Detection and analysis were completed with the ABI Prism™ Sequence Detection System. All amplification and detection reactions were completed in MOT. The average ΔRQ values for each dilution were plotted against the average CFU/ml as determined by plating each dilution on CT-SMAC. The adjusted ΔRQ threshold value was calculated to be 1.04 (dashed line). Error bars indicate the standard deviation of the mean (n=6).

Presumptive identification of *Escherichia coli* O157:H7 is possible in an individual, non-multiplexed PCR, if the reaction targets the enterohemorrhagic *E. coli* (EHEC) eaeA gene. The present invention describes the development and evaluation of the sensitivity and specificity of a PCR-based 5' nuclease assay for presumptively detecting *E. coli* O157:H7 DNA. The specificity of the eaeA-based, 5' nuclease assay system was sufficient to correctly identify all *E. coli* O157:H7 strains evaluated. The SZ-primed, eaeA-targeted, 5' nuclease detection assay was capable of rapid, semiautomated, presumptive detection of *E. coli* O157:H7 when $\geq 10^3$ CFU/ml were present in modified tryptic soy broth (mTSB) or modified *E. coli* broth (mEC), and when $\geq 10^4$ CFU/ml were present in ground beef-mTSB mixtures. Incorporating an immunomagnetic separation step (IMS), followed by a secondary enrichment culturing step and with a QIAamp Tissue Kit (QIAGEN) DNA recovery, improved the detection threshold to $\geq 10^2$ CFU/ml. Surprisingly, immediately after IMS, the sensitivity of culturing on sorbitol MacConkey agar containing cefeximine and tellurite (CT-SMAC) demonstrated identifiable colonies only when $\geq 10^4$ CFU/ml were present in the sample. Several factors that might be involved in creating these "false negative" CT-SMAC culture results are discussed. The SZ-primed, eaeA-targeted, 5' nuclease detection system demonstrated that it can be integrated readily into standard culturing procedures, and that the assay could be useful as a rapid, automatable process for the presumptive identification of *E.* coli O157:H7 in ground beef, and in other food and environmental samples.

The present invention is directed to a method of presumptively detecting E. coli O157:H7 using SZ-primed, eaeA-based 5' nuclease assay, comprising the steps of collecting a sample suspected to contain E. coli O157:H7; preparing an enrichment broth culture of the sample; extracting DNA from the culture; amplifying the DNA by PCR using E. coli O157:H7-specific primers; detecting the sample for E. coli O157:H7 by adding a fluorogenic probe specific for E. coli O157:H7 to the same reaction tube where the DNA was amplified; and analyzing the result to determine the presence or absence of E. coli O157:H7 DNA in the test sample. Preferably, the E. coli O157:H7-specific primers are SZ-I (SEQ ID NO: 1) and SZ-II (SEQ ID NO: 2). More preferably, the fluorogenic probe specific for E. coli O157:H7 targets the eaeA gene of E. coli O157:H7 and is selected from the group consisting of SEQ ID NO: 3 and SEQ ID NO: 4. Most preferably, SZI-97 (SEQ ID NO: 3) is the optimal probe.

In one preferred embodiment of the present invention, the sample is selected from the group consisting of a fecal sample, a n environmental sample, a food sample, veterinary sample and a medical diagnostic sample.

In another preferred embodiment of the present invention, the claimed method is automatable and detects $\geq 10^2$ CFU/ml of E. coli O157:H7 from the test sample. Generally, the entire identification process including extracting, amplifying and detecting steps takes approximately 2.5 hours.

The following examples are given for the purpose of illustrating various embodiments of the invention and are not meant to limit the present invention in any fashion.

EXAMPLE 1
Bacterial Strains and Culture Conditions

The strains of bacteria that were evaluated are listed in Table 1. The E. coli O157:H7, MD 380-94 strain, originally recovered from salami by the United State Department of Agriculture (USDA)-Food Safety Inspection Service (FSIS) after an associated disease outbreak, was used as the reference strain in all optimization and sensitivity experiments. The E. coli strains were cultured in modified E. coli broth (mEC, BBL, Cockeysville, Md.) containing 20 m g novobiocin/l or in tryptic soy broth (TSB, Difco, Detroit, Mich.) modified (mTSB) to contain 100 mg/l novobiocin, 10 mg/l cefsulodin, 8 mg/l vancomycin, and 0.05 mg/l cefeximine. All antibiotics were obtained from Sigma Chemical Co., St. Louis, Missouri. Cultures were transferred to plates of sorbitol MacConkey agar (SMAC, Difco) supplemented with cefeximine and tellurite (CT, Dynal, Lake Success, N.Y.) and incubated (18–24 h, 37° C.); these are referred to as CT-SMAC plates.

TABLE 1

Bacterial strains evaluated and the ΔRQ values generated in PCR with the SZ-I and SZ-II primers and the SZI-97 fluorogenic probe

| Bacterial Strains Evaluated | ΔRq[a] | "Yes" or "No" Interpretation[b] |
|---|---|---|
| E. coli O157:H7 | | |
| 43888[c] | 3.84 | yes |
| 43889[c] | 3.74 | yes |
| 43890[c] | 4.51 | yes |
| 43894[c] | 4.41 | yes |
| 43895[c] | 4.50 | yes |
| 88.1558[d] | 3.98 | yes |
| MD 380-94[e] | 2.77 | yes |
| meat isolate[e] [KSU label, Eh 7-1] | 4.19 | yes |
| 15753, meat isolate[e] | 4.16 | yes |
| 45756, meat isolate[e] | 3.48 | yes |
| 4731A, meat isolate[e] | 4.09 | yes |
| 45953, clinical isolate[f] | 4.29 | yes |
| 45959, clinical isolate[f] | 3.72 | yes |
| EDL 933, clinical isolate[f] | 4.47 | yes |
| Other E. coli Strains | | |
| E. coli O157:NM, MF7123A[e] | −0.02 | no |
| E. coli O157:NM, MF13180-25[e] | 4.01 | yes |
| E. coli O111:NM, 91.1030[d] | 0.06 | no |
| E. coli O11:NM, 90-1772[d] | 0.13 | no |
| E. coli O55:H7, Dec 5A[g] | 4.07 | yes |
| E. coli O55:H7, Dec 5B[g] | 4.68 | yes |
| E. coli, 11775[c] | 0.01 | no |
| E. coli, RCR93[h] | 0.07 | no |
| E. coli, 4221, canine isolate[i] | 0.08 | no |
| E. coli, 4225, canine isolate[i] | 0.35 | no |
| E. coli, 17/2[j] | 0.10 | no |
| E. coli, 2748/69[j] | 0.23 | no |
| E. coli, R555-1[j] | 0.17 | no |
| E. coli, 274-1[j] | 0.39 | no |
| E. coli, H10407[j] | −0.02 | no |
| E. coli, O26:H1[j] | 0.08 | no |
| E. coli, O5:NM[j] | −0.02 | no |
| E. coli, O6:H31[j] | −0.03 | no |
| E. coli, O26:H11[j] | −0.06 | no |
| E. coli, O103:H2[j] | −0.05 | no |
| E. coli, O111:NM[j] | −0.02 | no |
| E. coli, 862, porcine isolate[i] | 0.03 | no |
| E. coli, (O157 +; H7 −; sorbitol +; MUG +) 35A[e] | 0.24 | no |
| E. coli, (O157 −; H7 +) WS-41[f] | 0.07 | no |
| Other Bacteria | | |
| Hafnia alvei, 13337[c] | −0.08 | no |
| Citrobacter freundii, CL 787B-75[k] | 0.09 | no |
| C. freundii CL350B-77[k] | 0.01 | no |

[a]ΔRQ's determined with ~150 ng of template DNA from each strain in PCR conditions with 40 nM SZI-97 probe, and 2 mM MgCl₂ in two-step PCR in MOT with optical caps. [b]A yes score is assigned when the ΔRQ is greater than the ΔRQ threshold value calculated at the 99% confidence level, or ΔRQ >1.04. [c]American Type Culture Collection [d]E. coli Reference Center, Penn State University, Penn. [e]USDA, FSIS, Beltsville, Md. [f]Centers for Disease Control and Prevention, Atlanta, Ga. [g]Michael Doyle, University of Georgia, Athens, Ga. [h]Stan Bailey, Russell Research Center, Athens, Ga. [i]Bradley Fenwick, Kansas State University [j]David Acheson, Tufts University School of Medicine, Boston, Mass. [k]M.M. Chengappa, Veterinary Diagnostic Laboratory, Kansas State University.

EXAMPLE 2
Developing Fluorogenic Probes for E. coli O157:H7

Fluorogenic probes to the eaeA gene contained within the SZ-primed amplicon (41,42) (GenBank accession number U32312) were synthesized as previously described (2). The efficiency of individual probes was determined in PCR using purified DNA templates (QIAamp Tissue Kit, QIAGEN, Inc., Chatsworth, Calif.) from reference strains of E. coli and other bacteria. Approximately 150 ng of DNA (DNA Dip-Stick Kit, Invitrogen, Carlsdad, Calif.) from each reference strain of bacteria was PCR amplified using the E. coli O157:H7-specific primers, SZ-I (SEQ ID NO: 1) and SZ-II (SEQ ID NO: 2) (41,42). Following the two-step PCR, the fluorescence intensity of the fluorescent reporter dye (6-carboxy-fluorescein; $\lambda_{em}$=518) and the fluorescent quencher dye (6-carboxytetram-ethyl-rhodamine; $\lambda_{em}$=582) were determined for each tube by using a luminescence spectrometer with a 96-tube reader accessory (TaqMan® LS-50B PCR Detection System, Perkin-Elmer). The degree of hydrolysis was calculated using the equation, $\Delta RQ=RQ^+-RQ^-$ (2), where $$RQ^+ = \frac{\text{Emission of reporter dye}}{\text{Emission of quencher dye}}$$

$$RQ^- = \frac{\text{Emission of reporter dye (no DNA template)}}{\text{Emission of quencher dye (no DNA template)}}$$

The $\Delta RQ$ threshold for determining the presence ("yes") of *E. coli* O157:H7 DNA in individual MicroAmp Optical Tubes and Caps (MOT) (Perkin-Elmer) was based on a 99% confidence interval utilizing the standard deviation of $RQ^-$ values from no-template controls from >20 plates (3 no-template controls/plate). A "yes" interpretation of a $\Delta RQ$ value using MicroAmp Optical 96-Well Reaction Plates with MicroAmp Caps (MORP) (Perkin-Elmer) was determined at 99% confidence intervals using the standard deviation of $RQ^-$ values of 3 no-template controls per plate. Data were collected and analyzed using the Fluorescence Data Manager (Perkin-Elmer) and EXCEL spreadsheets (Microsoft Corporation, Redmond, Wash.) on a personal computer.

EXAMPLE 3

PCR Conditions

The PCR amplification conditions were modified from Meng et al. (41) and included fluorogenic probes. Briefly, 5 µl of sample containing the DNA template to be evaluated was added to 45 µl of PCR master mix [5 µl 1×PCR buffer II (Perkin-Elmer); MgCl$_2$ (from 1.5 to 4.0 mM); 200 nM of each primer (SZ-I, i.e, SEQ ID NO: 1 and SZ-II, i.e., SEQ ID NO: 2); 200 µM of dNTP; 0.025 U AmpliTaq DNA polymerase (Perkin-Elmer ); 25 to 50 nM fluorogenic probe; and 2 6 µl water] in 200 µl capacity MOT or in individual wells of a MORP. Each set of reactions included a single tube (well) of TE buffer (10 mM Tris-HCl pH 8.0, 1 mM EDTA) for the autozero control and triplicate tubes (wells) that were no-template controls (containing no *E. coli* O157:H7 DNA templates). Additional non-*E. coli* DNA was collected from other bacterial strains were included in each assay (*Salmonella cholerasuis, Hafnia alvei, Citrobacter freundii*, and NovaBlue, a general-purpose cloning host [Novagen, Madison, Wis.]). All non-*E.coli* organisms were cultivated in tryptic soy broth (37° C., overnight). The PCR had an initial denaturization step (95° C., 5 min) followed by 35 amplification cycles of a two-step PCR (95° C., 20 sec; 60° C., 60 sec), with a final extension (72° C., 10 min or longer) on a thermocyclet (GeneAmp® PCR System 9600, Perkin-Elmer).

EXAMPLE 4

DNA Recovery Procedures

To evaluate the sensitivity of an *E. coli* O157:H7 5' nuclease assay system, different DNA recovery procedures were evaluated with different types of samples.

QIAamp Tissue Kit

The ability of the QIAamp Tissue Kit to recover *E. coli* O157:H7 DNA from pure broth cultures was evaluated according to the manufacturer's instructions. Ten-fold dilutions were made of *E. coli* O157:H7 in mTSB. A 1.0 ml aliquot from each dilution was removed and pelleted by centrifugation (16,000×g, 10 min), and the supernatant was carefully removed and discarded. The pellets were centrifuged again (16,000×g, 1 min), and each pellet was resuspended in 180 µl of Buffer ATL (QIAGEN) and 20 µl of proteinase K stock solution (QIAGEN). Tubes were vortexed and incubated in a 55° C. waterbath for 30 min or until the sample was lysed. Twenty microliters of RNase A (20 mg/ml) was added to each tube, and the tubes were vortexed (5 sec) and incubated (room temperature, 2 min). Then 200 µl of Buffer AL (QIAGEN) was added to each tube, and tubes were vortexed (5 sec) and incubated (70° C. in a dry heating block, 10 min). Next, 210 µl of 100% ethanol was added to each tube, and the contents were mixed by vortexing and transferred to a QIAamp spin column that w as placed in a 2 ml collection tube.

The spin column and collection tube were centrifuged (5,200×g, 1 min). The spin column then was placed on a new collection tube, and 500 µl of Buffer AW (QIAGEN) was added to the column. The spin column and a new collection tube then were centrifuged (5,200×g, 1 min), the spin column was removed and placed into a new 2 mL collection tube, and 500 µl of Buffer AW was added. The spin column and a new collection tube were centrifuged (5,200×g, 1 min, followed by 16,000×g, 2 min), the spin columns then were placed onto marked 1.5 ml microcentrifuge tubes, and 200 µl of 70° C. Buffer $\Delta E$ (QIAGEN) was added. The liquid in the collection tubes was precipitated with ethanol and placed in QIAamp spin columns and processed according to the manufacturer's instructions. The DNA was eluted from the QIAamp spin columns by adding 200 µl of Buffer AE preheated to 70° C., incubating the columns at room temperature for 1 min, and then centrifuging the columns (6,000×g for 1 min). The resulting elution samples were stored at −20° C. or used in 5' nuclease assays.

DNA Extraction Reagent (DNA-ER) Procedure

One of the DNA recovery procedures evaluated utilized the chelating properties of chelex resin as previously described for recovering Salmonella DNA from foods (DNA Extraction Reagent Method, TaqMan® Salmonella PCR Amplification/Detection Kit, Perkin-Elmer). Briefly, 10-fold serial dilutions were made of mTSB and mEC broth cultures. Aliquots of 500 and 1,000 µl from each dilution were centrifuged (16,000×g, 3 min); the supernatant was decanted carefully; and the spellet was resuspended in 200 µl of thoroughly mixed DNA-ER solution (DNA Extraction Reagent, P/N N808-0087, Perkin-Elmer). The tubes were vortexed for 5–10 sec or as long as required to resuspend the pellet. The tubes then were incubated in a water bath (56° C., 30 min), floated in boiling water (7 min), and chilled on ice (5 min). The tubes then were centrifuged (16,000×g, 3 min), and the supernatants carefully transferred to new microcentrifuge tubes. A 5 µl aliquot of the supernatant served as the template for each PCR amplification in the 5' nuclease assay.

EXAMPLE 5

Sample Types

To evaluate the sensitivity of an *E. coli* O157:H7 5' nuclease assay, different sample types were evaluated.

Pure Cultures

Pure cultures of *E. coli* O157:H7 were 110 grown in mTSB or mEC (35° C., 12–15 hr). Ten-fold serial dilutions of the cultures were made using broth as the diluent, and aliquots were taken for *E. coli* O157:H7 enumeration (CFU/ml) on CT-SMAC and for immediate DNA recovery.

Immunomagnetic Separation from Pure Cultures

*Escherichia coli* O157:H7 was detected and enumerated following recovery by immunomagnetic separation (IMS) from mTSB using the beads as inoculum for direct plating onto CT-SMAC, using the beads as inoculum for secondary enrichment and subsequent plating onto CT-SMAC, or recovering DNA from each of the previous steps and subjecting it to *E. coli* O157:H7 5' nuclease reactions.

Specifically, 10-fold dilutions were made of pure cultures of *E. coli* O157:H7 while they were in logarithmic growth (between 4–8 hr old cultures). Aliquots of broth (100 µl) were plated on CT-SMAC plates in triplicate (incubated 37° C., 18 hr). Similarly, 0.5 and 1.0 ml aliquots were collected and subjected to the DNA-ER and QIAamp Tissue Kit DNA extraction methods. Simultaneously, 1.0 ml aliquots were collected from each dilution and transferred to microcentrifuge tubes containing 20 µl of a-*E. coli* O157 immunomagnetic beads (Dynabeads® Anti-*E. coli* O157, Dynal, Inc., Lake Success, N.Y.). The beads were separated using a stationary magnet and washed according to the manufacturer's instructions and then placed in 200 µl phosphate buffered saline. These bead solutions then were equally divided: 100 µl was plated on CT-SMAC (incubated 37° C., 18 h), and 100 µl was added to a tube containing 9.0 ml of mTSB for secondary enrichment culturing (37° C., 18 h). Following secondary enrichment incubation, 100 µl aliquots of each dilution were plated on CT-SMAC (37° C., 18 h), and 0.5 and 1.0 ml aliquots were collected and subjected to both the DNA-ER and QIAamp Tissue Kit DNA recovery procedures. DNA also was recovered from 0.5 and 1.0 ml aliquots immediately prior to IMS and following 18 h secondary enrichment of IMS beads, then subjected to 5' nuclease assay. The resulting ΔRQ values obtained from each dilution were compared with the CT-SMAC culture results. All 5' nuclease assay reactions in the IMS study were conducted in 96-well MORP.

Ground Beef Samples Spiked with *E. coli* O157:H7

The ability to detect *E. coli* O157:H7 in ground beef was evaluated by spiking ground beef samples with different numbers of bacteria, then recovering DNA from each spiked sample and subjecting it to the 5' nuclease detection assay. Ground beef (containing 20% fat) was obtained from the Kansas State University Meat Processing Laboratory on three different occasions and confirmed to be culture negative for *E. coli* O157:H7 before inclusion in the study. *Escherichia coli* O157:H7 (MD 380-94) was collected from mTSB cultures while it was in logarithmic growth (4–8 h), and 10-fold dilutions were made in mTSB. One milliliter of each dilution was added to tubes containing 9.0 ml ground beef-mTSB mixture (10 g ground beef, 90 ml mTSB) that had been previously incubated (6 h, 37° C.). Aliquots (0.5 ml) were immediately removed from each dilution for DNA recovery using the DNA-ER procedure and the QIAamp Tissue Kit, and then subjected to the 5' nuclease assay. All 5' nuclease assay reactions containing ground beef were conducted in 96-well MORP.

EXAMPLE 6

*E. coli* O157:H7 Fluorogenic TagMan Probe Design, 5' Nuclease Assay Performance, and Specificity The adaptation of a 5' nuclease fluorogenic detection process to a PCR specific for *E. coli* O157:H7 required the evaluation of DNA sequences upstream of the eaeA gene. Recommended guidelines for designing fluorogenic probes for 5' nuclease assays were followed (35), and four fluorogenic probes (SZI-97, SZI-107, SZII-194, SZII-200, i.e., SEQ ID NOs: 3–6) targeting both complementary DNA strands of the SZ-primed amplicon were constructed using standard procedures (Table 2). Unless otherwise noted, all specificity evaluations were conducted in MOT.

TABLE 2

Primers and fluorogenic probes

| Primers | Sequence (5'→3') | | $T_d$(° C.)[b] | Location Within eaeA gene[c] |
|---|---|---|---|---|
| SZ-I | CCATAATCATTTTATTTAGAGGGA | SEQ ID NO: 1 | 61.7 | 28–51 |
| SZ-II | GAGAAATAAATTATATTAATAGATCGGA | SEQ ID NO: 2 | 61.6 | 632–659 |
| Probes[d] | | | | |
| SZI-97 | TTGCTGCAGGATGGGCAACTCTTGAp | SEQ ID NO: 3 | 78 | 97–121 |
| SZI-107 | ATGGGCAACTCTTGAGCTTCTGTAAp | SEQ ID NO: 4 | 70.3 | 107–131 |
| SZII-194 | ATTGTCGCTTGAACTGATTTCCTCp | SEQ ID NO: 5 | 74.3 | 582–605 |
| SZII-200 | TAATGTTTATTGTCGCTTGAACTGATp | SEQ ID NO: 6 | 66.4 | 588–613 |

[a]Primer sequences as described by Meng et al. (1996).
[b]Denaturation temperature ($T_d$) calculated by nearest-neighbor algorithm.
[c]*E. coli* 0157:H7 intimin (eaeA) gene as described in GenBank accession U32312.
[d]Phosphoramidites added to the 5' end [Fluorescent reporter dye (6-FAM)] and the 3' end [fluorescent quencher dye (TAMARA)]. The 3' end also contained a phosphate cap (p).

The efficiency of the probes was evaluated in PCRs with DNA recovered from reference strains of *E. coli* O157:H7, other *E. coli* strains, and other bacteria. In preliminary evaluations, the SZI-97 (SEQ ID NO: 3) and SZI-107 (SEQ ID NO: 4) fluorogenic probes generated higher ΔRQ values (Table 3). Based of these findings, the SZI-97 probe was selected as the probe for optimization and further evaluation of the 5' nuclease assay. Monitoring ΔRQ values in PCRs with varying concentrations of the SZI-97 probe (25–50 nM) identified 35 nM as the optimal probe concentration for all subsequent PCRs (data not shown). Similarly, the $MgCl_2$ concentration was shown to influence the ΔRQ value, and subsequent PCRs utilized a final concentration of 4 mM $MgCl_2$ (Table 4).

TABLE 3

Evaluating probes for the *E. Coli* O157:H7 PCR-based fluorogenic 5' nuclease assay

| Bacterial DNA Template | ΔRQ Values for Probes[a]/"Yes or No" Interpretation[b] | | | |
|---|---|---|---|---|
| | SZI-97 | SZI-107 | SZII-94 | SZII-200 |
| NovaBlue Competent Cells[c] | −0.02/no | 0.03/no | 0.03/no | −0.12/no |
| *E. coli* O157:H7[d] | 1.28/yes | 1.21/yes | 1.02/yes | 1.19/yes |
| *E. coli* O157:NM[e] | 0.08/no | −0.05/no | −0.05/no | −0.08/no |
| *E. coli* O157:H7[f] | 2.03/yes | 2.24/yes | 1.53/yes | 1.74/yes |
| *E. coli* O111:NM[g] | 0.07/no | −0.03/no | 0.03/no | 0.00/no |
| *E. coli* O157:NM[h] | 2.51/yes | 2.00/yes | 1.56/yes | 1.75/yes |
| *E. coli* O111:NM[i] | 0.04/no | −0.02/no | −0.01/no | −0.11/no |
| *Salmonella cholerasuis*[j] | 0.04/no | 0.03/no | 0.12/no | −0.05/no |

[a]Probes at 40 nM final concentration in MOT for two-step/cycle PCR using SZ primers and approx 150 ng of purified template DNA (QIAamp Tissue Kit) in each reaction.
[b]A yes score is assigned when the ΔRQ is greater than the ΔRQ threshold value (1.04) calculated at the 99% confidence levels.
[c]NovaBlue pET Host Strain Genotype (endAl hsdR17(rk−, mk+) supE44 thi-1 gyrA96 relAl lac [F', proAB, lacl$^q$XΔM15, Tn10(tet$^r$)] recAl), Novagen, Inc., Madison, Wisc.
[d]*E. coli* O157:H7, MD380–94, USDA, FSIS, Beltsville, Md.
[e]*E. coli* O157:NM, MF7123DS, USDA, FSIS, Beltsville, Md.
[f]*E. coli* O157:H7, 88.1588, *E. coli* Reference Center, Penn State University, Penn.
[g]*E. coli* O111:NM, 91.1030, *E. coli* Reference Center, Penn State University, Penn.
[h]*E. coli* O157:NM, MF13180-25, USDA, FSIS, Beltsville, Md.
[i]*E. coli* O111:NM, 90-1772, *E. coli* Reference Center, Penn State University, Penn.
[j]*S. cholerasuis*, 94-00041, Veterinary Diagnostic Laboratory, Kansas State University.

TABLE 4

Effect of MgCl2 concentration on ΔRQ values with the SZ primers and SZI-97 fluorogenic probe

| Bacterial Strain | ΔRQ Values with Varying [$MgCl_2$][a] | | |
|---|---|---|---|
| | 1.5 mM | 2.5 mM | 4.0 mM |
| *E. coli* O157:H7, MD380-94[b] | 1.42 | 1.64 | 4.82 |
| *E. coli* O157:H7, 88.1558[c] | 0.65 | 1.32 | 5.58 |
| *E. coli* O157:NM, MF7123A[d] | 0.15 | 0.09 | 0.6 |
| *E. coli* O111:NM, 91.1030[e] | −0.18 | −0.02 | 0.47 |
| *E. coli* O157:NM, MF13180-25[b] | 1.22 | 1.46 | 4.74 |
| *E. coli* O111:NM, 90-1772[d] | −0.35 | 0.17 | 0.06 |
| NovaBlue Competent Cells[e] | 0.17 | 0.0 | −0.03 |
| *Salmonella cholerasuis*[f] | −0.18 | 0.34 | 0.0 |

[a]Using approx 150 ng DNA extracted with QIAamp ® Tissue Kit in two-step, SZ-primed PCR with 40 nM of SZI-97 probe in MOT.
[b]USDA, FSIS, Beltsville, Md.
[c]American Type Culture Collection
[d]*E. coli* Reference Center, Penn State University, Penn.
[e]NovaBlue pET Host Strain Genotype (endAl hsdR17(rk−, mk+) supE44 thi-1 gyrA96 relAl lac [F', proAB, Tn10(tetT)] recAl), Novagen, Inc., Madison, Wisc.
[f]*S. cholerasuis*, 94-00041, Veterinary Diagnostic Laboratory, Kansas State University.

Similar to the PCR results described by Meng et al. (41), elevated ΔRQ values were demonstrated in all PCRs that used the SZ primers, 35 nM of the SZI-97 probe (SEQ ID NO: 3), and ~150 ng *E. coli* O157:H7 DNA (Table 1). Utilizing a ΔRQ detection threshold level determined at 99% confidence limits, all *E. coli* O157:H7 strains evaluated in MOT demonstrated ΔRQ values that were greater than the ΔRQ threshold level ($\geq 2.04$) and, therefore, resulted in "yes" conclusions for the presence of *E. coli* O157:H7 DNA in the sample. The ΔRQ detection threshold level indicative of a "yes" conclusion using MORP at 99% confidence limits was $\geq 0.34$.

In evaluations of the specificity of the SZ primers (SEQ ID NOs: 1–2) and the fluorogenic SZI-97 probe (SEQ ID NO: 3) for organisms other than *E. coli* O157:H7, ΔRQ values above the detection threshold were observed with some *E. coli* O157:NM strains and two enteropathogenic *E. coli* O55:H7 strains (Table 1). This cross-reactivity was similar to that described by Meng et al. (41,42) using the SZ primers in single and multiplex PCRs. No elevated ΔRQ values above threshold detection limits were detected for the other reference bacteria, including *H. alvei* or *C. freundii* strains.

Sensitivity of the *E. coli* O157:H7 5' Nuclease Detection System. The sensitivity of the *E. coli* O157:H7 fluorogenic 5' nuclease detection system using DNA recovered with the QIAamp Tissue Kit from overnight cultures of *E. coli* O157:H7 grown in either mTSB or mEC and with PCRs conducted and analyzed in MOT resulted in ΔRQ values greater than the detection threshold level when (104 CFU/ml were present (FIG. 1). The sensitivity of the 5' nuclease assay was increased when the PCRs and detection/analysis were conducted in MORP (Table 5). The minimum ΔRQ levels indicative of a "yes" conclusion using the MORP were recorded when $\geq 10^3$ CFU/ml of *E. coli* O157:H7 in logarithmic growth were evaluated. This detection level was demonstrated using both the QIAamp Tissue Extraction Kit and the DNA-ER procedure (Table 5).

TABLE 5

Comparison of standard culture and the E. coli O157:H7 5' nuclease assay ΔRQ values for detecting E. coli O157:H7 using different DNA extraction procedures and at different times before and after immunomagnetic separation (IMS)

| CFU[a], immed. before IMS | DNA-ER[b] ΔRQ[c] Values | | | | QIAamp[d] ΔRQ Values | | | | CFU, after IMS[e] | CFU, IMS +18h[f] |
|---|---|---|---|---|---|---|---|---|---|---|
| | Before IMS- 1.0 ml[g] | Before IMS- 0.5 ml | IMS +18h- 1.0 ml | IMS +18h- 0.5 ml | Before IMS- 1.0 ml | Before IMS- 0.5 ml | IMS +15h- 1.0 ml | IMS +18h- 0.5 ml | | |
| $3.3 \times 10^7$ | 7.79 | 7.79 | 4.72 | 6.07 | 6.97 | 7.16 | 8.07 | 7.54 | $1.7 \times 10^6$ | $2.8 \times 10^6$ |
| $1.7 \times 10^6$ | 7.31 | 6.90 | 0.41 | 1.18 | 5.98 | 6.14 | 7.61 | 7.48 | $7.2 \times 10^5$ | $1.8 \times 10^6$ |
| $2.1 \times 10^5$ | 5.66 | 5.34 | 0.32 | 0.27 | 4.21 | 4.86 | 7.42 | 6.79 | $4.8 \times 10^4$ | $9.4 \times 10^3$ |
| $1.6 \times 10^4$ | 2.99 | 3.04 | 6.27 | 6.23 | 2.53 | 2.01 | 8.30 | 7.96 | $2.0 \times 10^3$ | $2.7 \times 10^5$ |
| $1.8 \times 10^3$ | 0.71 | 1.05 | 0.04 | 0.03 | 0.93 | 0.64 | 6.76 | 6.31 | ND[h] | $1.5 \times 10^3$ |
| $9.8 \times 10^1$ | 0.06 | 0.19 | 0.00 | 0.05 | 0.15 | 0.15 | 6.91 | 6.25 | ND | $2.2 \times 10^1$ |
| $2.0 \times 10^1$ | −0.01 | 0.02 | −0.02 | 0.02 | 0.02 | 0.09 | 0.03 | −0.03 | ND | ND |
| $1.0 \times 10^1$ | −0.03 | 0.07 | −0.01 | 0.00 | 0.03 | −0.01 | 0.05 | 0.02 | ND | ND |

[a]CFU/ml (average 3 plates) determined by plating 0.1 ml mTSB with E. coli O157:H7 (MD 380-94) on CT-SMAC agar plates (incubated 37° C., 18 h).
[b]DNA Extraction Reagent-based DNA extraction (DNA-ER) procedure as described in Salmonella TaqMan Kit, Perkin-Elmer.
[c]All PCRs and analyses were conducted in MicroAmp Optical 96-well Reaction Plates (MORP) (Perkin-Elmer). ΔRQ detection threshold for "yes" respondents had ΔRQ ≧0.34.
[d]QIAamp Tissue Extraction Kit, QIAGEN, Inc.
[e]Dynabead ® Anti-O157, Dynal, Inc., 20 μl washed beads resuspended to 100 μl with TE buffer.
[f]Following IMS, beads were incubated in 9.0 ml mTSB (incubated 37° C., 18 h).
[g]Volume of mTSB extracted (0.5 or 1.0 ml).
[h]ND, not detected.

Figure 2:
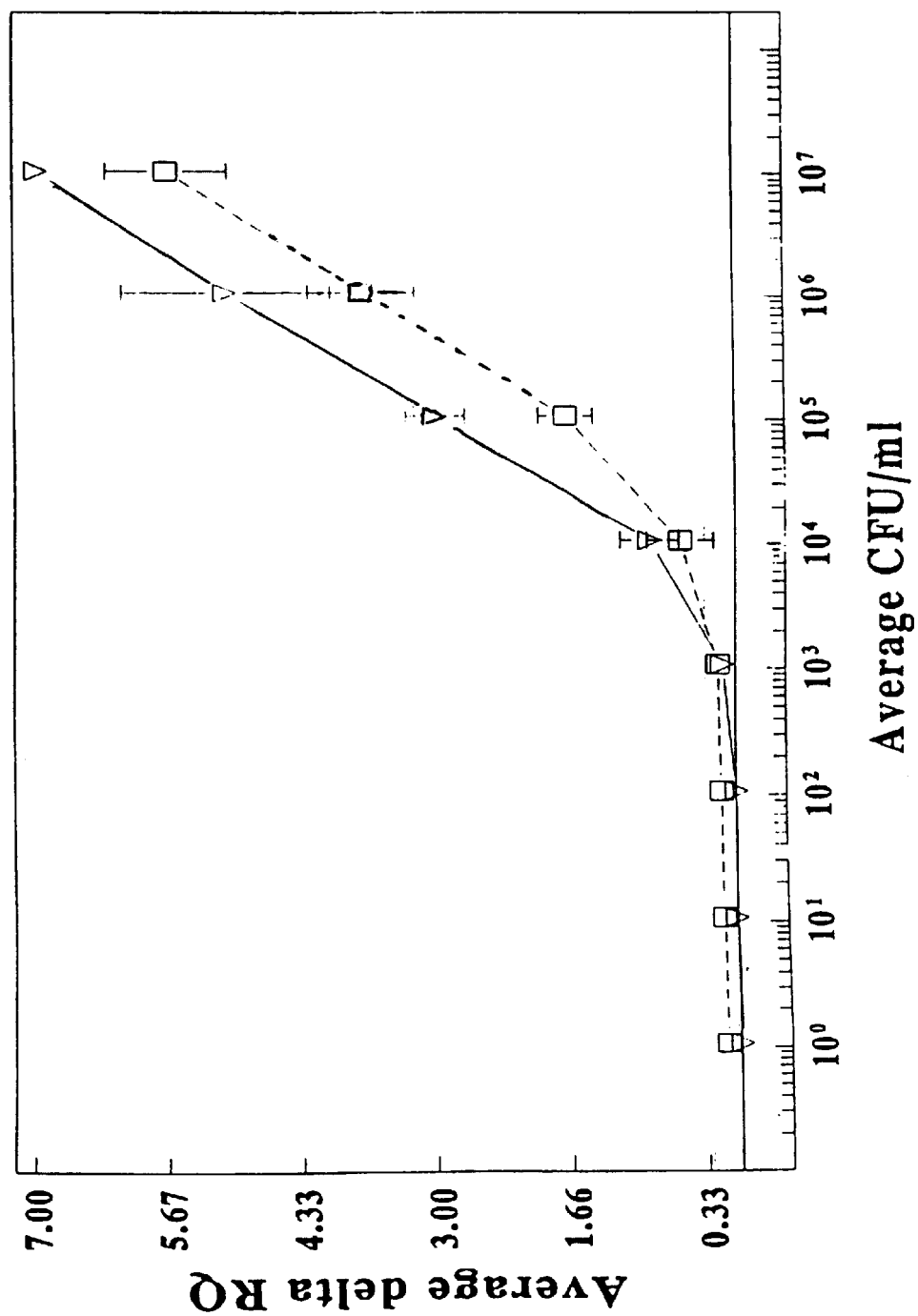
FIG. 2 shows sensitivity of the fluorogenic 5' nuclease assay for detecting *E. coli* O157:H7 in modified tryptic soy broth (mTSB) containing ground beef. Ten-fold dilutions of *E. coli* O157:H7 were made in mTSB in triplicate and 1.0 ml added to a tube containing 9.0 ml ground beef-mTSB mixture (10 g ground beef, 90 ml mTSB, incubated 6h, 37° C.). Aliquots (0.5 ml) were collected for DNA recovery using the DNA-ER (®) and the QIAamp Tissue Kit (∇) DNA extraction methods and 5 μl of the recovered DNA solution was amplified with the SZ-I (SEQ ID NO: 1) and SZ-II (SEQ ID NO: 2) primers in the presence of the SZI-97 fluorogenic probe. Detection and analysis were completed with the ABI Prism™ Sequence Detection System. All amplification and detection reactions were completed in MORP. The average ΔRQ values determined from DNA recovered from both DNA extraction methods were plotted against the average CFU/ml determined by plating each ground beef dilution on CT-SMAC. The ΔRQ threshold value at 99% confidence limits was calculated to be 0.34. Error bars indicate the standard deviation from the mean (n=3).

Sensitivity of the 5' nuclease assay to identify E. coli O157:H7 was found to be approximately 1 O° CFU/ml in ground beef-mTSB mixtures (FIG. 2). The ΔRQ values obtained from various dilutions of ground beef-mTSB mixtures were indicative of a "yes" conclusion (ΔRQ values ≧0.33) when ≧$10^4$ CFU/ml were processed in 0.5 ml aliquots with the QIAamp Tissue Extraction Kit. This sensitivity was obtained without including an IMS step. Using the same dilutions, the DNA-ER procedure demonstrated similar "yes" and "no" conclusions but gave consistently lower average ΔRQ values than the QIAamp Tissue Extraction Kit when ($10^4$ CFU/ml were present (FIG. 2).

A difference was noted in the ΔRQ values when samples containing older cultures of E. coli O157:H7 were processed using the two DNA recovery methods. The DNA recovered with the QIAamp Tissue Extraction Kit after IMS-18 h secondary enrichment demonstrated ΔRQ values interpreted as "yes" when the starting inoculum was ≧$10^2$ (9.8×101) CFU/ml (Table 5). This was also the limiting dilution at which E. coli O157:H7 was recovered on CT-SMAC following IMS-18 h secondary enrichment. The ΔRQ values obtained from the same dilutions but utilizing the DNA-ER recovery process gave "yes" conclusions when the starting inoculum prior to IMS was ≧$10^4$ CFU/ml. However, the ΔRQ values obtained using the DNA-ER procedure were inconsistent and resulted in numerous false negative "no" interpretations, as determined by plating of IMS-18 h secondarily enriched dilutions on CT-SMAC and recovering organisms at the dilutions when the starting inolculum contained ≧$10^2$ CFU/ml. Decreasing the volume of the secondary enrichment media processed for DNA recovery did not appear to improve the efficiency of the DNA-ER procedure, because interpretations of ΔRQ values were similar whether 1.0 or 0.5 ml were processed (Table 5).

EXAMPLE 7

Discussion

The ability to presumptively detect E. coli O157:H7 DNA from diverse kinds of samples using an automated amplification/detection procedure would be beneficial to food producers, food processors, food safety regulatory agencies, and clinical microbiologists. The present invention describes the development and evaluation of a PCR-based, 5' nuclease (TaqMan™) assay for automatically amplifying and then detecting E. coli O157:H7 DNA. The ability of the assay to detect E. coli O157:H7 DNA was successful, with "yes" interpretations for all reference strains of E. coli O157:H7 evaluated; for pure cultures of E. coli O157:H7 grown in mTSB and mEC; and for ground beef-mTSB mixtures spiked with E. coli O157:H7. Detection sensitivities were improved if IMS and 18 h secondary enrichments were incorporated into the process.

The data indicate that the automated eaeA-based E. coli O157:H7 5' nuclease detection assay, when integrated with an effective DNA recovery process, is capable of rapid, semiautomated, presumptive detection of E. coli O157:H7 if ≧$10^3$ CFU/ml are present in mTSB or mEC, or ≧$10^4$ CFU/ml in a ground beef-mTSB mixture. These data also indicate that incorporating pre- and secondary enrichment steps and an IMS recovery process could further improve the sensitivity of the detection procedure. Because only 1/40th of a 1.0 ml sample (concentrated to 200 μl following DNA recovery) was actually evaluated in any PCR (5 μl sample/PCR), evaluating a larger fraction of the sample per PCR or further concentrating the DNA in the sample potentially could increase the sensitivity of the procedure. However, both steps would increase costs or add additional manipulations to the procedure.

The strategy for developing an E. coli O157:H7-specific fluorogenic probe was to target an internal region of the SZ-primed amplicon that could detect subtle sequence differences between the eaeA gene of E. coli O157:H7 and similar genes in enteropathogenic E. coli, C. freundii, and H. alvei. Specificity of the fluorogenic probe in this PCR was based on the presumptions that an increase in reporter fluorescence emission from the probe would occur only if, the PCR primers would anneal specifically to E. coli O157:H7 DNA templates as previously described (41,42)

and simultaneously, the fluorogenic probe would anneal specifically to the same target that contained the eaeA gene of *E. coli* O157:H7 and that digestion of the probe would occur only if extension of the new complementary strand of DNA proceeded in a 5'→3' as predicted in a successful PCR.

Utilizing the SZ-I (SEQ ID NO: 1) and SZ-II (SEQ ID NO: 2) primers in PCR in the presence of the fluorogenic SZI-97 probe (SEQ ID NO: 3, in MOT), it was possible to presumptively determine the presence of *E. coli* O157:H7 DNA in broth cultures of mTSB and mEC with similar sensitivity ($\geq 10^4$ CFU/ml). The sensitivity was increased to $\geq 10^3$ CFU/ml using MORP and was comparable to the previously reported sensitivity of the SZ-primed eaeA-based PCR as determined by visually interpreting ethidium bromide-stained agarose gels (41). The difference in sensitivities between MOT and MORP was attributed to improved reproducibility of the optical characteristics of MORP, resulting in more consistent $\Delta RQ^-$ values, which, in turn, reduced the $\Delta RQ$ detection threshold level. Regardless, all *E. coli* O157:H7 strains evaluated demonstrated $\Delta RQ$ values above the detection threshold levels and resulted in "yes" interpretations at 99% confidence levels.

Elevated $\Delta RQ$ values above the detection threshold were also observed with some *E. coli* O157:NM strains and two enteropathogenic *E. coli* O55:H7 strains. These findings were not unexpected, because similar cross-reactivity has been demonstrated using the SZ primers in single and multiplex PCRs (41,42). In most circumstances, cross-reactivity in a PCR would be sufficient to limit the usefulness of those primers for detection purposes; however, several points suggest that the SZ-primed, eaeA-based, 5' nuclease detection system would be useful as a rapid, sensitive, semiautomated, presumptive detection process for *E. coli* O157:H7 in food and environmental samples. First, the eaeA-based, 5' nuclease assay system was able to correctly identify all *E. coli* O157:H7 strains evaluated. Secondly, all cross reactivity was limited to organisms that would be considered as human pathogens and undesirable in foods. Specifically, *E. coli* O157:NM has been increasingly isolated from hemolytic uremic syndrome patients in Europe (8,26), and the enteropathogenic *E. coli* O55:H7 is associated with worldwide outbreaks of infantile diarrhea (52). Phylogenetic analyses have also suggested that *E. coli* O157:H7 might have originated from an *E. coli* O55:H7 clone (52).

Regardless, definitive confirmation could be completed by standard culture techniques on all presumptive "yes" samples identified by the SZ-primed, 5' nuclease assay. Similarly, all presumptive "yes" samples could be confirmed by PCR amplification/detection approaches targeting eaeA and the sltI-sltII genes as described by Meng et al. (41,42). The latter approach would eliminate the need to complete biochemical or immunological analyses to correctly confirm the identity of *E. coli* O157:H7 isolates. Once identified by the presumptive eaeA-based 5' nuclease assay, efforts to recover viable organisms from the broth culture could b e initiated using standard techniques. For example, once sorbitol non-fermenting colonies were identified on CT-SMAC, confirmatory *E. coli* O157:H7 genetic testing could be initiated on colonies using fluorogenic 5' nuclease detection systems that individually targeted the eaeA, the sltI and sltII genes with specific fluorogenic probes (28,41,42).

Perhaps the most important attribute of the eaeA-based 5' nuclease assay for presumptively detecting *E. coli* O157:H7 is that the entire identification process (disregarding culture incubation times) takes approximately 2.5 hr (about 20 minutes for DNA recovery, <2 hr for PCR preparation and thermal cycling, and <15 min for PCR product detection and analysis).

Sample processing is an important component of any DNA-based detection system. To optimize sample preparation, the ability of two extraction procedures was analyzed to recover *E. coli* O157:H7 DNA for the 5' nuclease detection system. When *E. coli* O157:H7 cultures in logarithmic growth were evaluated, the DNA-ER and the QIAamp Tissue Kit DNA extraction methods were equally effective in demonstrating "yes" $\Delta RQ$ values (read in MORP) if $\geq 10^3$ CFU/ml were present. However, when older cultures (IMS plus 18 h secondary enrichment) were evaluated, the efficiency of the DNA-ER procedure as determined by $\Delta RQ$ values, demonstrated differences that could be associated only with the DNA recovery processes. When DNA was recovered with the DNA-ER procedure, $\Delta RQ$ values of samples containing older cultures were highly variable. This variability hindered interpretation of the end-point sensitivity of the assay and, more importantly, resulted in false-negative interpretations when compared to CT-SMAC culture results. When the QIAamp Tissue Kit was evaluated using the same dilutions, the $\Delta RQ$ values and "yes" interpretations were identical to the IMS plus 18 h secondary enrichment culture results on CT-SMAC, indicating a detection capability when $\geq 10^2$ CFU/ml were present in the original dilution.

The 5' nuclease detection system was able to detect *E. coli* O157:H7 when $\geq 10^3$ CFU/ml were present in pure culture in mTSB or mEC and were comparable to the results Meng et al. (41) obtained visually interpreting agarose gels. However, incorporating an IMS step, followed by a secondary enrichment culturing step and QIAamp Tissue Kit DNA recovery, improved the detection threshold to $\geq 10^2$ CFU/ml in the original sample. This detection level is closer to the suggested minimum infectious dosage for humans (25,53).

Surprisingly, the sensitivity of CT-SMAC culturing immediately after IMS resulted in identifiable colonies only if $\geq 10^4$ CFU/ml were present in the original sample. Several factors might be involved in creating these "false negative" culture results. First, the detection limits of the IMS procedure using Dynabeads Anti-*E. coli* O157 beads is approximately 102 organisms/ml of pre-enriched sample (Dynal), indicating that *E. coli* O157:H7 concentrations <$10^2$ CFU/ml could go undetected. Also, the successful isolation of some strains of *E. coli* O157:H7 could be affected adversely by plating onto CT-SMAC. A recent study indicated that plating unstressed, laboratory-reared *E. coli* O157 isolates on CT-SMAC adversely affected their isolation by delaying their growth and resulting in false negative conclusions (39). Surprisingly, organisms were able to be detected in dilutions that originally contained >$10^2$ and <$10^4$ CFU/ml, only when they were subjected to IMS and an additional 1 8 h secondary enrichment prior to being plated on CT-SMAC. To overcome this delay in growth and improve the recovery for some *E. coli* O157 strains, it has been suggested reducing the levels of antibiotics in pre-enrichment broths prior to IMS and plating on CT-SMAC (9,39.

In order to demonstrate the applicability of a presumptive *E. coli* O157:H7 5' nuclease detection system in food production and processing facilities, throughput capability of the system can be enhanced by integrating automated liquid handling capability into the process, automating the DNA recovery process, and linking all phases of the integrated detection process with a computer-based system that would allow increased retrieval and storage of data. As demonstrated in this study, presumptive pathogen detection systems utilizing 5' nuclease assay components can be integrated readily into standard culture/detection procedures to reduce the time required to presumptively detect *E. coli*

O157:H7 or other microbial contaminates. Cost and time savings could also be realized by reducing the need for complete bacterial isolation procedures and biochemical/immunological characterizations on every sample, unless suggested by an eaeA-based 5' nuclease assay presumptive "yes" result.

The following references were cited herein.
1. Alexander, E. R., 1995. Morbid. Mortal. Weekly Rep. 44:157–159.
2. Bassler, H. A., et al., 1995. Appl. Environ. Microbiol. 61:3724–3728.
3. Basta, M., et al., 1989. J. Clin. Microbiol. 27:1617–1622.
4. Batt, C. A. 1997. J. Dairy Sci. 80:220–229.
5. Belongia, E. A., et al., 1991. J. Infect. Dis. 164:338–343.
6. Bennett, A. R., et al., 1996. Letters Appl. Microbiol. 22:237–243.
7. Besser, R. E., et al., 1993. JAMA 269:2217–2220.
8. Bitzan M., et al., 1993. Epidemiol. Infect. 110:183–196.
9. Bolton, F. J., et al., 1996. Letters Appl. Microbiol. 23:317–321.
10. Cebula, T. A., et al., 1995. J. Clin. Microbiol. 33:248–250.
11. Chapman, P. A., et al., 1994. J. Med. Microbiol. 40:424–427.
12. Chapman, et al., 1997. Appl. Environ. Microbiol. 63:2549–2553.
13. Chen S., et al., 1997. Int. J. Food Microbiol. 35:239–250.
14. Coleman, D. J., et al., 1995. Letters Appl. Microbiol. 21:249–251.
15. Como-Sabetti, et al., 1997, Morbid Mortal. Weekly Rep. 46:741–744.
16. Cubbon, M. D., et al., 1996. J Med. Microbiol. 44:219–222.
17. Donohue-Rolfe, A., et al., 1989. Infect. Immun. 57:3888–3893.
18. Dorn C. R. 1993. J. Am. Vet. Med. Assoc. 203:1583–1587.
19. Doyle, M. P. 1991. Int. J. Food Microbiol. 12:289–302.
20. Faith N. G., et al., 1996. Appl. Environ. Microbiol. 62:1519–1525.
21. Farmer, J. J., et al., 1985. J. Clin. Microbiol. 22:620–625.
22. Fratimico, P. M., et al., 1992. Food Microbiol. 9:105–113.
23. Fratimico, P., et al., 1995. J. Clin. Microbiol. 33:2188–2191.
24. Garber, L. P., et al., 1995. J. Am. Vet. Med. Assoc. 207:46–49.
25. Griffin P., et al., 1991. Epidemiol. Rev. 13:60–98.
26. Gunzer F., et al., 1992. J. Clin. Microbiol. 30:1807–1810.
27. Hancock, D. D., 1994. Epidemiol. Infect. 113:199–207.
28. Ho, et al., 1997, Abstr. P-17, p. 439. In Abstracts of the 97th Meeting of the American Society of Microbiology, Washington, D.C.
29. Holland, et al., 1991. Proc. Natl. Acad. Sci. USA 88: 7276–7280.
30. Johnson, R. P., et al., 1995. Appl. Environ. Microbiol. 61:386–388.
31. Karch, H., et al., 1996. J. Clin. Microbiol. 34:516–519.
32. Karch, H., et al., 1989. J. Clin. Microbiol. 27:2751–2757.
33. Kleanthous, H., et al., 1988. Epidemiol. Infect. 101:327–335.
34. Lee, L. G., et al., 1993. Nucl. Acid Res. 21:3761–3766.
35. Livak K. J., et al., 1995. PCR Methods Appl. 4:357–362.
36. Louie, M., et al., 1994. Epidemiol. Infect. 112:449–461.
37. Lyamichev, V., et al., 1993. Science 260: 778–783.
38. Matsuura M., et al., 1997. Am. Environ. Lab. March 24–25.
39. MacRae, M., et al., 1997. Letters Appl. Microbiol. 25:135–137.
40. Mechie, S. C., et al., 1997. Epidemiol. Infect. 118:12–25.
41. Meng, J., et al., 1996. Int. J. Food Microbiol. 32:103–113.
42. Meng, J., et al., 1997. Letters Appl. Microbiol. 24:172–176.
43. O'Brien, A. D., et al., 1993. J. Clin. Microbiol. 31:2799–2801.
44. Okrend, A. J. G., et al., 1992. J. Food Prot. 55:214–217.
45. Padhye, N. V., et al., 1991. J. Clin. Microbiol. 29:99–103.
46. Park, C. H., et al., 1996. J. Clin. Microbiol. 34:988–990.
47. Paton, A. W., et al., 1993. J. Clin. Microbiol. 31:3063–3067.
48. Sanderson, M. W., et al., 1995. J. Clin. Micobiol. 33:2616–2619.
49. Sernowski, L. P., et al., 1992. J. Food Prot. 55:846.
50. Vanderzant, C., et al., 1992. Compendium of methods for microbiological examination of foods, 3rd ed. Edward Brothers, Ann Arbor, Mich.
51. Venkateswaran, et al., 1997. Appl. Environ. Micro. 63:4127–4131.
52. Whittam, T. S., et al., 1993. Infect. Immun. 61:1619–1629.
53. Willshaw, G. A., et al., 1994. Lett. Appl. Microbiol. 19:304–307.
54. Witham, et al., 1996. Appl. Environ. Microbiol. 62:1347–1353.
55. Zhao, T., et al., 1995. Appl. Environ. Microbiol. 61:1290–1293.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of determining whether a sample is free of the presence of *E. coli* O157:H7 using an eaeA-based 5' nuclease assay, wherein SZ primers are used as a nuclease target in said assay, comprising the steps of:
   collecting a sample to be tested for the possible presence of *E. coli* O157:H7;
   preparing an enrichment broth culture of said sample;
   extracting DNA from said culture;
   amplifying said DNA by PCR using *E. coli* O157:H7 eaeA-specific primers, wherein said primers amplify all or part of a sequence corresponding to nucleotides 28 to 659 of GenBank accession number U32312 in the presence of a fluorogenic probe specific for an *E. coli* O157:H7 eaeA-specific sequence positioned between said primers, wherein said fluorogenic probe is selected from the group consisting of SZI-97 having SEQ ID NO: 3 and SZI-107 having SEQ ID NO-4; and
   analyzing the fluorescence of said sample, wherein an increase in fluorescence indicates the possible presence of *E. coli* O157:H7 in said sample, and no increase in fluorescence indicates that the sample is free of *E. coli* O157:H7.

2. The method of claim 1, wherein said *E. coli* O157:H7-specific primers are selected from the group consisting of SZ-I having SEQ ID NO: 1 and SZ-II having SEQ ID NO: 2.

3. The method of claim 1, wherein said probe is SZI-97 having SEQ ID NO: 3.

4. The method of claim 1, wherein said sample is selected from the group consisting of a fecal sample, a n environmental sample, a food sample, a veterinary sample and a medical diagnostic sample.

5. The method of claim 1, wherein said method is automated.

6. The method of claim 1, wherein the identification process including said extracting and amplifying steps takes less than 3.0 hours.

7. The method of claim 1, wherein said method detects $\geq 10^2$ CFU/ml of *E. coli* O157:H7 from said sample.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: artificial sequence
<220> FEATURE:
<221> NAME/KEY: primer_bind
<222> LOCATION: 28..51
<223> OTHER INFORMATION: E.coli O157:H7 eaeA gene specific PCR primer
      SZ-I
<300> PUBLICATION INFORMATION:
<301> AUTHORS: Meng, J.
      Zhao, S.
      Doyle, M. P.
      Mitchell, S. E.
      Kresovich, S.
<302> TITLE: Polymerase chain reaction for detecting Escherichia
      coli O157:H7
<303> JOURNAL: Int. J. Food Microbiol.
<304> VOLUME: 32
<305> ISSUE:
<306> PAGES: 103-113
<307> DATE: 1996

<400> SEQUENCE: 1
ccataatcat tttatttaga ggga                                          24

<210> SEQ ID NO 2
<211> LENGTH: 28
<212> TYPE: DNA
<213> ORGANISM: artificial sequence
<220> FEATURE:
<221> NAME/KEY: primer_bind
<222> LOCATION: 632..659
<223> OTHER INFORMATION: E.coli O157:H7 eaeA gene specific PCR primer
      SZ-II
<300> PUBLICATION INFORMATION:
<301> AUTHORS: Meng, J.
      Zhao, S.
      Doyle, M. P.
      Mitchell, S. E.
      Kresovich, S.
<302> TITLE: Polymerase chain reaction for detecting Escherichia
      coli O157:H7
<303> JOURNAL: Int. J. Food Microbiol.
<304> VOLUME: 32
<306> PAGES: 103-113
<307> DATE: 1996

<400> SEQUENCE: 2
gagaaataaa ttatattaat agatcgga                                      28

<210> SEQ ID NO 3
<211> LENGTH: 25
<212> TYPE: DNA
<213> ORGANISM: artificial sequence
<220> FEATURE:
<222> LOCATION: 97..121
<223> OTHER INFORMATION: E.coli O157:H7 specific fluorogenic probe SZI-
      97 targeting the eaeA gene

<400> SEQUENCE: 3
ttgctgcagg atgggcaact cttga                                         25

<210> SEQ ID NO 4
<211> LENGTH: 25
<212> TYPE: DNA
<213> ORGANISM: artificial sequence
<220> FEATURE:

```
<221> NAME/KEY: primer_bind
<222> LOCATION: (107)...(131)
<223> OTHER INFORMATION: E.coli O157:H7 specific fluorogenic probe SZI-
      107 targeting the eaeA gene

<400> SEQUENCE: 4
atgggcaact cttgagcttc tgtaa                                          25

<210> SEQ ID NO 5
<211> LENGTH: 24
<212> TYPE: DNA
<213> ORGANISM: artificial sequence
<220> FEATURE:
<221> NAME/KEY: primer_bind
<222> LOCATION: 582..605
<223> OTHER INFORMATION: E.coli O157:H7 specific fluorogenic probe SZII-
      194 targeting the eaeA gene

<400> SEQUENCE: 5
attgtcgctt gaactgattt cctc                                           24

<210> SEQ ID NO 6
<211> LENGTH: 26
<212> TYPE: DNA
<213> ORGANISM: artificial sequence
<220> FEATURE:
<222> LOCATION: 588..613
<223> OTHER INFORMATION: E.coli O157:H7 specific fluorogenic probe SZII-
      200 targeting the eaeA gene

<400> SEQUENCE: 6
taatgtttat tgtcgcttga actgat                                         26
```